United States Patent [19]

Murphy

[11] Patent Number: 5,346,997
[45] Date of Patent: Sep. 13, 1994

[54] AGENTS FOR COMPLEXING SODIUM UNDER BIOLOGICAL CONDITIONS

[76] Inventor: James G. Murphy, 820 Robert St., Venice, Fla. 34285

[21] Appl. No.: 935,571

[22] Filed: Aug. 26, 1992

[51] Int. Cl.$^5$ .................. C07G 3/00; C07G 11/00; A01N 43/04; A61R 31/70
[52] U.S. Cl. .................................................. 536/4.1
[58] Field of Search ........................ 536/4.1; 514/25

[56] References Cited

U.S. PATENT DOCUMENTS

| | | | |
|---|---|---|---|
| 2,938,911 | 5/1960 | Linn | 424/480 |
| 3,185,682 | 5/1965 | Sarett et al. | 424/180 |
| 3,240,777 | 3/1966 | Sarett et al. | 424/180 |
| 3,621,005 | 11/1971 | Ishidate et al. | 424/180 |
| 3,852,435 | 12/1974 | Tamura | 424/180 |
| 3,880,995 | 4/1975 | Jones | 424/180 |
| 4,337,760 | 7/1982 | Rubin | 424/180 |
| 4,481,195 | 11/1984 | Rubin | 424/180 |
| 4,553,972 | 11/1985 | Vickery | 424/430 |
| 4,637,985 | 1/1987 | Sidki et al. | 436/518 |
| 4,900,730 | 2/1990 | Miyauchi | 424/436 |
| 4,956,355 | 9/1990 | Prendergast | 514/178 |
| 4,992,259 | 2/1991 | Schiraldi et al. | 424/642 |
| 5,013,724 | 5/1991 | Petitou et al. | 514/54 |
| 5,098,692 | 3/1992 | Gries et al. | 424/9 |

*Primary Examiner*—Nathan M. Nutter
*Attorney, Agent, or Firm*—Gifford, Groh, Sprinkle, Patmore and Anderson

[57] ABSTRACT

An agent for complexing sodium in aqueous solution comprises a glucuronic acid, specifically, beta-d-glucopyranosiduronic acid. The agent of the present invention furthermore includes the salts and esters of beta-d-glucopyranosiduronic acid. The salt of this acid is the triethanolamine salt of benzyl beta-d-glucopyranosiduronic acid. The ester of this acid is the benzyl ester. The agent of the present invention complexes sodium in aqueous solution in the pH range of living systems. Accordingly, it has use against such maladies as hypertension when taken internally and baldness when applied topically using a carrier in oil form.

7 Claims, 1 Drawing Sheet

AGENTS FOR COMPLEXING SODIUM UNDER BIOLOGICAL CONDITIONS

BACKGROUND OF THE INVENTION

I. Field of the Invention

The present invention relates to agents for complexing sodium under biological conditions. More particularly, the present invention relates to benzyl beta-d-glucopyranosiduronic acid and the salts and esters thereof as agents for complexing sodium. The present invention also relates to a method of synthesizing these agents and to their uses in biological systems.

II. Description of the Relevant Art

Living organisms require large quantities of sodium to maintain normal body function. Sodium chloride satisfies an essential mineral need that must be constantly replenished. For example, an adult human must consume about three grams of NaCl daily. Even more of this mineral must be consumed if vigorous activity is undertaken.

Human blood plasma has a very high concentration of sodium which, for the most part, is contained within extracellular fluids ( 142.0 m Eq/l as compared with 10.0 m Eq/l in intracellular fluids) . High concentrations of positively charged ions, such as sodium ($Na^+$), potassium ($K^+$), and calcium ($Ca^{+2}$) are particularly important in, for example, the conduction of nerve impulses, the contraction of muscle fibers, and for maintaining the normal permeability of cell membranes.

When nerve cells are at rest, the concentration of sodium ions on the outside of the cell membrane is greater than on the inside. The opposite is true for potassium ions. Large numbers of negatively charged ions are provided within the cytoplasm. Because cell membranes are slightly permeable to sodium ions and are highly permeable to potassium ions , the latter tend to diffuse freely through the membrane to the outside, while the sodium ions tend to diffuse slowly into the cell. Because the cell membrane expends energy during active transport to carry these ions in opposite directions, equilibrium is not reached, and as a result, sodium ions are actively transported outward through the membrane, while potassium ions are transported inward. The net effect of this transaction is for more positively charged ions to leave the cell than to enter it, and the outside of the membrane becomes positively charged with respect to the negative charge on the outside.

Sodium ions account for nearly 90% of the positively charged ions in extracellular fluid. The primary regulation mechanism that regulates the numbers of sodium ions involves the kidneys and the hormone aldosterone. This hormone is secreted by the adrenal cortex. This system does not, however, always operate in proper balance.

As is so often the case in the event of hypertension, increased levels of angiotensin, a powerful vasoconstrictor, results in increases in the peripheral resistance in the arterial system. This causes the arterial pressure to rise.

Angiotensin also causes aldosterone to be released from the adrenal cortex. Because the hormone promotes the retention of sodium ions and water by the kidneys, the resulting increase in blood volume causes an additional increase in blood pressure.

Other problems are attendant excess sodium ions in relation to the human body. For example, hair loss is thought to be related to the presence of an overabundance of sodium ions on the skin.

Accordingly, a method and composition is wanting that would safely reduce the number of excess sodium ions in the body while operating within the pH range of living systems . This is true because , while it is known that complexing agents and chelating agents are a valuable group of compounds (for example, versenes) , complexing agents for sodium ion are rare. Such rarities include, for example, crown ethers. However, while it is true that complexing agents for sodium ion are rare, complexing agents for sodium ion that function under physiological conditions are even more rare.

SUMMARY OF THE PRESENT INVENTION

The present invention relates to an agent for complexing sodium in aqueous solution within the pH range of living systems. The present invention also relates to a method of production of such agents and methods of medicinal administration.

The agent of the present invention includes glucuronide agents useful for complexing sodium ion under aqueous biological conditions. Specifically, this agent comprises benzyl-beta-d-glucopyranosiduronic acid. The agent of the present invention furthermore includes the salts and esters of benzyl-beta-d-glucopyranosiduronic acid. The salt of this acid is the triethanolamine salt of benzyl beta-d-glucopyranosiduronic acid. The ester of this acid is the benzyl ester. Glucuronides are valuable as the agent of the present invention in that they are not metabolized and are not rapidly excreted.

The present invention is directed to the relief of hypertension, cystic fibrosis, and baldness. In the first two conditions, the sodium-complexing agent is provided for internal use. In the last-mentioned condition, the agent is provided with a carrier such as oil for topical application. In all cases the present invention resolves problems commonly associated with irregularities in sodium metabolism by providing an agent to modulate sodium concentration.

By complexing sodium ions, the agent of the present invention serves to relieve the affected system from the effects of overabundance of the ions. This removal promotes the return to proper balance of the system.

Accordingly, as will be shown below, the present invention provides a complexing agent for the sodium ion that functions under physiological conditions, such conditions being in water and at a mildly alkaline pH.

BRIEF DESCRIPTION OF THE DRAWINGS

The present invention will be more fully understood by reference to the following detailed description of the preferred embodiment when read in conjunction with the accompanying drawings, in which like characters refer to like parts throughout the views, and in which.

DETAILED DESCRIPTION OF THE PREFERRED EMBODIMENTS OF THE PRESENT INVENTION

Figure 1:
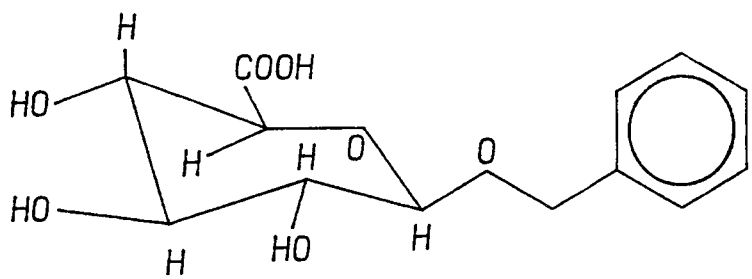
FIG. 1 is the structure of benzyl-beta-d-glucopyranosiduronic acid as discussed in the present application.

Glucuronic acid is a compound ($C_6H_{10}O_7$) that occurs most commonly as a constituent of mucopolysaccharides (such as hyaluronic acid). D-glucuronic acid has been found to be catabolized only slightly in certain animals. This is thought to be due to the non-penetration of D-glucuronic acid into cells. The structure of the benzyl-beta-d-glucopyranosiduronic acid is set forth in FIG. 1.

A glucuronide is a carbohydrate and is one of many possible derivatives of glucuronic acid that is commonly formed as combinations with harmful substances. Such harmful substances include often toxic aromatic hydroxyl compounds (such as phenols). The combination is removed from the body in the urine.

The first report on a glucuronide was published in 1855. That glucuronide, Indian yellow, was identified as a urinary conjugate taken from cows fed mango leaves.

Beyond their value in this neutralizing capacity, glucuronides are believed capable of complexing cations. Accordingly, euxanthic acid is believed to complex magnesium, and phenethyl-beta-d-glucopyranosiduronic acid has been shown to complex copper.

The present invention relates to the use of benzyl beta-d-glucopyranosiduronic acid to complex sodium in aqueous sol ut ion at about pH 8.

Conventional methods for the synthesis of beta-d-glucopyranosiduronic acids are known. One of the earliest descriptions of a method of synthesis was set forth by C. Neuberg & W. Neimann (*Z. Phsiol. Chem.* 44, 114 [1905]). The success of this work, however, was never confirmed.

Set forth below are examples of the successful synthesis of the benzyl ester of benzyl beta-d-glucopyranosiduronic acid, the triethanolamine salt of benzyl beta-d-glucopyranosiduronic acid, and their uses as agents for complexing sodium ions.

SYNTHESIS OF THE AGENTS

Examples

Process for Synthesizing the Benzyl Ester of beta-d-Glucopyranosiduronic Acid

According to this example, d-glucuronolactone was reacted with benzyl alcohol using methanesulfonic acid as a catalyst. After neutralizing the acid and removal of the inorganics, the benzyl ester of benzyl beta-d-glucopyranosiduronic acid was obtained.

The specific formulation, quantities, and conditions follow. All listed parts are by weight.

A 0.48 part of methanesulfonic acid and 1.76 parts of d-glucuronolactone was added to 2.16 parts of benzyl alcohol. The mixture was stirred for a 24-hour period. At the end of stirring, 1.26 parts of sodium bicarbonate were introduced. A resulting foam was allowed to subside. The mixture was then diluted with ethyl acetate. After dilution, the mixture was filtered.

Evaporation of the filtrate gave 3.22 parts of pale yellow oil product. The product showed an Rf of 0.63 (silica gel chromatography, ethyl acetate development, thermal visualization at 260° C.) The yield was 86 percent.

Process for Synthesizing the Triethanolamine Salt of Benzyl beta-d-Glucopyranosiduronic Acid According to this example, the above-identified esteruronide hydrolyzed readily in the presence of triethanolamine to give the TEA salt of benzyl beta-d-glucopyranosiduronic acid. The hydrolysis solution was evaporated in a vacuum over silica gel.

The specific formulation, quantities, and conditions follow. All listed parts are by weight.

A mixture of 0.149 parts triethanolamine, 2.55 parts of water and 0.37 parts of the benzyl ester of benzyl beta-d-glucopyranosiduronic acid was stirred at room temperature for six hours. The resulting solution was near colorless and was evaporated in a vacuum over silica gel. The product was 0.42 parts of syrup and showed an Rf of 0.42 (silica gel, 3 methanol:5 ethyl acetate development, thermal visualization at 320° C.) The yield was 98 percent.

RESULTS

The TABLE set forth below lists the results of titrating a 0.33M solution of benzyl beta-d-glucopyranosiduronic acid with 0.1M sodium chloride. The benzyl ester of benzyl beta-d-glucopyranosiduronic acid, 0.30 ml, was hydrolyzed in 0.70 ml of water and 2.0 ml, of 0.5M triethanolamine. The resulting solution was titrated with 0.1M sodium chloride. This titration was done using an ion selective electrode that measured the free sodium ion at each point. The results disclose that the amounts of free sodium found were very different from the amounts of sodium added.

TABLE

| ml/0.1M NaCl added | Calculated [Na+] | Found [Na+] |
|---|---|---|
| 1 | 0.025 | 0.0011 |
| 2 | 0.04 | 0.0040 |
| 3 | 0.05 | 0.0082 |
| 4 | 0.057 | 0.016 |
| 5 | 0.0625 | 0.025 |
| 6 | 0.067 | 0.037 |
| 7 | 0.07 | 0.046 |
| 8 | 0.073 | 0.053 |
| 9 | 0.075 | 0.067 |
| 10 | 0.077 | 0.077 |
| 11 | 0.079 | 0.088 |
| 12 | 0.08 | 0.11 |

Figure 2:
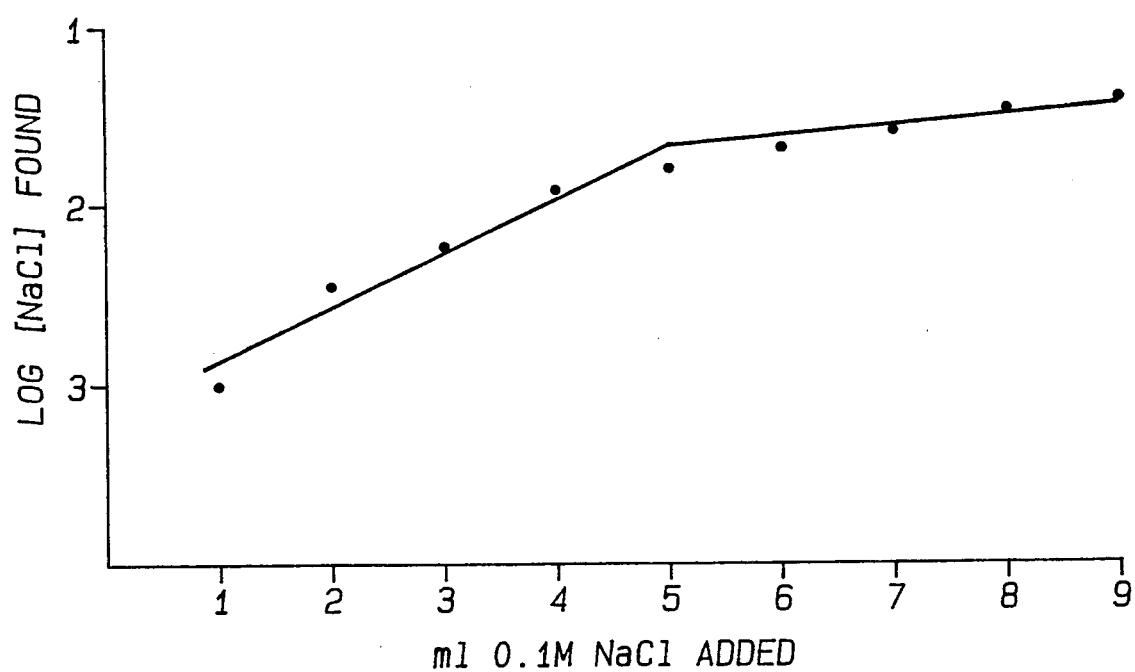
FIG. 2 is a graphical representation of the titration of a 0.33M solution of benzyl beta-d-glucopyranosiduronic acid with 0.1M sodium chloride as discussed in the "Results" section appearing below.

These results are presented graphically in FIG. 2. Two straight lines result which intersect at a ratio of two benzyl beta-d-glucuronic acid molecules to one sodium ion.

CLINICAL RESULTS

Because it is theorized that sodium ion accumulation at the skin surface represses hair growth, topical application of an agent according to the present invention was made to the scalp of a patient.

Two drops of a 4% mixture of the benzyl ester of benzyl beta-d-glucopyranosiduronic acid with sunflower as a carrier were applied to the hair line of the left temple of a 72-year old male subject. The mixture was applied to an approximately one-inch band behind the hair line. Application was continued once a day for a period of four months. Thickening of the hair along the temple hair line was observed after the end of this period.

The invention being thus described, it will be obvious that the same may be varied in many ways. Such variations are not regarded as a departure from the spirit and scope of the invention, and all such modifications are intended to be included within the scope of the following claims.

What is claimed is:

1. An agent for complexing sodium ions comprising a benzyl glucuronic acid, said benzyl glucuronic acid being beta-d-glucopyranosiduronic acid, said agent further comprising the salt and ester of said benzyl glucuronic acid, said agent being used in combination with an oil carrier for pharmaceutical applications.

2. An agent for complexing sodium ions, said agent comprising:
    benzyl beta-d-glucopyranosiduronic acid,
    the salt of benzyl glucuronic acid, and
    the ester of benzyl glucuronic acid,
    whereby said agent complexes sodium in aqueous solution in the pH range of between 6.0 and 8.0.

3. An agent for complexing sodium ions, said agent comprising:
    benzyl beta-d-glucopyranosiduronic acid,
    the salt of benzyl glucuronic acid, and
    the ester of benzyl glucuronic acid,
    whereby said agent when combined with an oil carrier complexes sodium in aqueous solution in the pH range of between 6.0 and 8.0.

4. An agent for complexing sodium ions, said agent comprising benzyl beta-d-glucopyranosiduronic acid, whereby said agent when combined with a carrier complexes sodium in aqueous solution in the pH range of between 6.0 and 8.0.

5. The agent of claim 4 further including the salt of benzyl glucuronic acid.

6. The agent of claim 4 further including the ester of benzyl glucuronic acid.

7. The agent of claim 5 further including the ester of benzyl glucuronic acid.

* * * * *